United States Patent [19]

Corpi Constantino

[11] Patent Number: 5,728,691
[45] Date of Patent: Mar. 17, 1998

[54] QUINOLONYLCARBOXAMIDOCEPHALOSPORIN DERIVATIVES AND PHARMACEUTICAL COMPOSITIONS CONTAINING THEM

[75] Inventor: Miguel Angel Corpi Constantino, Queretaro Qro, Mexico

[73] Assignees: Laboratorios Aranda S.A. De C.V., Queretaro Qro, Mexico; Judith Marcia Arrieta Munguia, Brussels, Belgium

[21] Appl. No.: 693,231

[22] PCT Filed: Oct. 7, 1994

[86] PCT No.: PCT/IB94/00304

§ 371 Date: Aug. 22, 1996

§ 102(e) Date: Aug. 22, 1996

[87] PCT Pub. No.: WO95/23153

PCT Pub. Date: Aug. 31, 1995

[30] Foreign Application Priority Data

| Feb. 25, 1994 | [MX] | Mexico | 941427 |
| May 6, 1994 | [MX] | Mexico | 943331 |
| May 9, 1994 | [MX] | Mexico | 943394 |
| Sep. 1, 1994 | [MX] | Mexico | 946680 |
| Sep. 1, 1994 | [MX] | Mexico | 946681 |
| Sep. 1, 1994 | [MX] | Mexico | 946682 |
| Sep. 5, 1994 | [MX] | Mexico | 947838 |

[51] Int. Cl.$^6$ ...................... C07D 501/36; A61K 31/545
[52] U.S. Cl. .................. 514/202; 514/203; 514/204; 514/205; 514/206; 514/207; 544/225; 544/227; 544/228; 544/222
[58] Field of Search ................... 540/225, 227, 540/228, 222; 514/202, 203, 204, 205, 206, 207

[56] References Cited

U.S. PATENT DOCUMENTS 4,404,201  9/1983  Haskell et al. ............... 425/246

FOREIGN PATENT DOCUMENTS

| A 0 062 328 | 10/1982 | European Pat. Off. . |
| A 251 330 | 1/1988 | European Pat. Off. . |
| A 0 304 158 | 2/1989 | European Pat. Off. . |
| A 0 366 193 | 5/1990 | European Pat. Off. . |
| A 0 591 808 | 5/1990 | European Pat. Off. . |

OTHER PUBLICATIONS

Arzneim.–Forsch./Drug. Res., vol. 29 (I), No. 2A, 1979, pp. 362–369. R. Gericke, W. Rogalski [New 4–Pyridonyl–acetamido–caphalosporins and Related Compounds].

J. Med.Chem., vol. 33, No. 1, 1990, pp. 77–86. H.A. Albrecht et al. [Cephalosporin 3'–quinolone Esters with a Dual Mode of Action].

J. Antibiot., vol. 44, No. 2, 1991, pp. 200–209. T.P. Demuth et al. [Synthesis and Antibacterial Activity of New C–10 Quinolonyl–Cephem Esters].

International Search Report dated Apr. 1, 1995 for PCT/IB94/00304.

*Primary Examiner*—John M. Ford
*Attorney, Agent, or Firm*—Armstrong, Westerman, Hattori, McLeland & Naughton

[57] ABSTRACT

Derivatives of 7-aminoceph-3-em-4-carboxylic acid with 6-fluoroquinolone derivatives in which the cephem and 6-fluoroquinolone moieties are bound to each other through a carboxamido bond as well as the pharmaceutical compositions containing them are described. These compounds possess antibacterial, growth promoting and probiotic activity.

22 Claims, No Drawings

QUINOLONYLCARBOXAMIDOCEPHALOSPORIN DERIVATIVES AND PHARMACEUTICAL COMPOSITIONS CONTAINING THEM

The present invention relates to quinolonylcarboxamidocephalosporin derivatives and to the pharmaceutical compositions having antibacterial activity which contain them.

The quinolonylcarboxamidocephalosporin derivatives of the invention are in particular derivatives of 7-aminoceph-3-em-4-carboxylic acid with 6-fluoroquinolone derivatives in which the cephem and 6-fluoroquinolone moieties are bound each other through a carboxamido bond. These compounds are also referred hereinafter as 'cefaquinolone derivatives'.

A further object of the invention relates to the process for the preparation of said derivatives.

The 6-fluoroquinolonylcarboxamidocephalosporin derivatives, or cephaquinolone derivatives of the present invention possess striking potency against a wide range of microorganisms, either gram-negative or gram-positive of extra or intra-cellular type as well as an interesting growth promoting and probiotic action.

DESCRIPTION OF THE INVENTION

The object of the present invention relates to 6-fluoroquinolonylcarboxamidocephalosporin derivatives, herewith also referred as cephaquinolone derivatives, to the process for their preparation and to the antibacterial, growth promoting and probiotic pharmaceutical compositions containing said compounds.

The 6-fluoroquinolonylcarboxamidocephalosporin derivatives of the invention are endowed with a very high antimicrobial activity effective against a wide range of gram-negative and gram-positive microorganisms and with an interesting growth promoting and probiotic action which activities render the present compounds useful in human and veterinarian applications.

More particularly the cephaquinolone derivatives of the invention have structure formula:

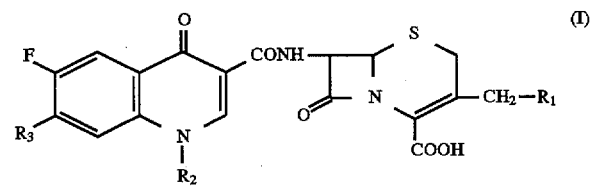

wherein
- $R_1$ represents hydrogen, acetoxy, carbamyloxy, an heterocyclic group selected among pyridin-1-yl, 1H-1,2,3-triazol-5-ylthio, 1-methyl-1H-tetrazol-5-ylthio, 5-methyl-1,3,4-thiadiazol-2-ylthio, 2,5-dihydro-6-hydroxy-2-methyl-5-oxo-1,2,4-triazin-3-ylthio;
- $R_2$ represents hydrogen, 1–4 C straight or branched alkyl radical, 3–5 C cycloalkyl radical;
- $R_3$ represents a halogen atom, an heterocyclic group selected among piperazin-1-yl, 4-methylpiperazin-1-yl, 4-ethylpiperazin-1-yl.

As 1–4 C straight alkyl radical is intended methyl, ethyl, propyl and butyl, ethyl being preferred. As 1–4 C branched alkyl radical are intended isopropyl, sec.butyl and tert.butyl, isopropyl being preferred. As 3–5C cycloalkyl radical is intended cyclopropyl, cyclobutyl and cyclopentyl, cyclopropyl being preferred.

As halogen atom bromine, fluorine and chlorine are intended, chlorine being preferred.

Also included in the scope of the present invention are the alkaline metal salts and the ammonium salt of the compounds of formula (I) which may be obtained according to well known procedures. Particularly preferred are the sodium, potassium and ammonium salts of the compounds of formula (I).

The compounds (I) of the invention in which $R_3$ represents a halogen atom are prepared by reacting the 6-fluoro-7-halo-1,4-dihydro-4-oxoquinoline-3-carboxylic acid (IV), in a suitable activated form (III), with the 7-aminoceph-3-em derivative (II) and optionally, when desired, introducing a substituent other than halide at position 7 of the quinolone moiety in compound (Ib).

In particular, in the case of an activated form represented by 6-fluoro-7-halo-1,4-dihydro-4-oxoquinoline-3-carbonyl chloride the process can be represented by the reaction scheme:

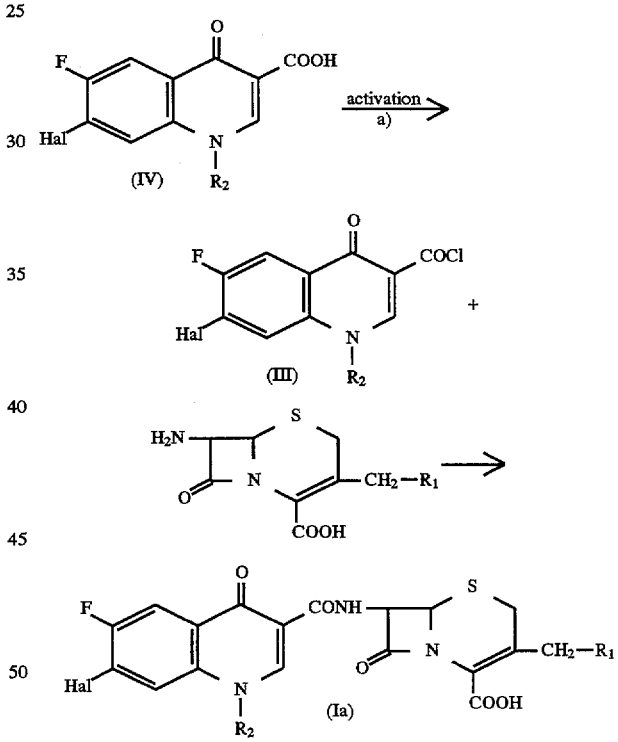

wherein $R_1$ and $R_2$ have the above mentioned meaning and Hal represents a halogen atom.

The compounds of formula (I) in which $R_3$ represents a piperazin-1-yl radical optionally 4-substituted with a methyl or ethyl radical are prepared from the corresponding 7-haloquinolonilcarboxamido-ceph-3-em derivative (Ia) by reacting with piperazine optionally 1-methyl or 1-ethyl-substituted according to the reaction:

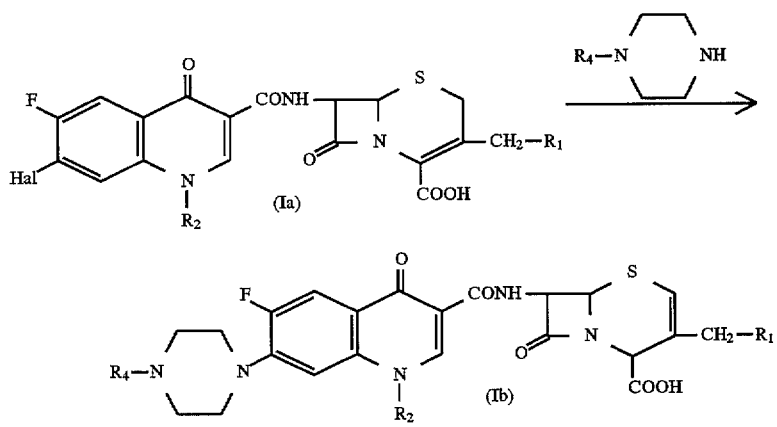

wherein Hal, $R_2$ and $R_1$ have the above mentioned meaning and $R_4$ is selected among hydrogen, methyl and ethyl.

In alternative to the above indicated form as acyl chloride, compound (IV) may be in the form of mixed anhydride with a suitable acid: these compounds may be obtained according to the method known in the art. In particular, as to compound (III) it may be easily prepared by reacting the corresponding acid (IV) with a suitable halogenating agent, such as thionyl chloride, phosphorus tri- or penta-chloride, in a suitable solvent such as toluene, benzene, methylene chloride, acetone, dimethylformamide or acetic acid.

The mixed anhydride of compound (IV) with a suitable acid may be prepared reacting at low temperature the corresponding compound (IV) potassium salt with the chloride of the selected acid, the preferred one being trimethylacetyl chloride.

Starting compounds (IV) may be prepared from the corresponding 1-unsubstituted quinolone-2-carboxylic acid (compound IV in which $R_2$ is hydrogen) by reaction with $R_2$ Hal in a suitable solvent in the presence of a suitable halogenhydric acid acceptor such as, for example, an alkaline carbonate or an organic base, preferably a trialkylamine or pyridine. As suitable solvent an organic polar solvent having a boiling point of approximately 100° C. may be used.

The compounds (I) of the present invention possess a very high antibacterial activity which is expressed against a wide range of either gram-negative or gram-positive microorganisms of extra or intracellular type as well as an interesting growth promoting and probiotic activities. They may be suitably mixed with pharmaceutically excipients and formulated in a suitable manner for oral, parenteral and topical administration. The pharmaceutical compositions, which contain as active principle an effective quantity of one or more compounds of formula (I) may be in the form of pills, tablets, dragées, granulates, powders, emulsions, solutions, foams, creams and suppositories.

The quantity of the active principle which is daily administered may vary depending on the type of the administration chosen, on the age and on the condition of the patient.

The following Examples are given to better illustrate the invention without limiting it.

EXAMPLE 1

7-[(1-Ethyl-6-fluoro-7-chloro-1,4-dihydro-4-oxoquinolin-3-yl) carboxyamido]cephalosporanic acid, and sodium salt.

Grams 26.9 of 1-ethyl-6-fluoro-7-chloro-1,4-dihydro-4-oxo-3-quinolinecarboxylic acid are added to 120 ml glacial acetic acid and the mixture, cooled to 15°-20° C., is stirred until complete dissolution. To this solution 65.6 g thionyl chloride are added dropwise in the period of 30 minutes while temperature is raised to 25°-30° C. The mixture is stirred for 6 hr. to 20°-25° C., then cooled to 10°-15° C. to separate under vacuum a crystalline compound consisting of 1-ethyl-6-fluoro-7-chloro-1,4-dihydro-4-oxo-3-quinolinecarboxyl chloride.

The so obtained product is washed with 250 ml dry benzene and to it 250 ml dry methylisobutylketone are added under stirring at 5° C. The mixture pH is adjusted to approximately 7 by addition of triethylamine.

Grams 25 of 7-aminocephalosporanic acid in 200 ml dimethylformamide are cooled under stirring to 10° C. and, keeping stirring on, 25 ml triethylamine are added until complete dissolution at 5° C. This solution is slowly added to the previously prepared 1-ethyl-6-fluoro-7-chloro-1,4-dihydro-4-oxo-3-quinolinecarboxyl chloride mixture maintained under stirring at 5° C., then the temperature is allowed to increase to 20°-25° C. and stirring is maintained for a further 2 hr. To the mixture are added 200 ml cold water, then pH is adjusted to 8.5-9 adding ammonium hydroxide and the mixture stirred until complete dissolution.

The solution obtained is filtered, the layers separated and the organic layer washed again with water, then the aqueous layers, collected together, are treated with activated carbon, filtered under vacuum, the temperature is cooled to 10°-15° C. and keeping under stirring, pH is adjusted to 4-5 by addition of hydrochloric acid. Stirring is maintained for a further 2 hr. A crystalline compound separates which is filtered under vacuum, washed with 200 ml water and 100 ml isopropanol to give 35.6 g 7-[(1-ethyl-6-fluoro-7-chloro-1,4-dihydro-4-oxoquinolin-3-yl)carboxyamido] cephalosporanic acid, mp 260°-280° C. (decomposition).

Grams 100 of this compound are suspended in 600 ml methylene chloride and 400 ml isopropanol and to the stirred mixture, cooled to 15° C., 70 ml triethylamine are added and stirring is maintained until complete dissolution. It is filtered under vacuum and to the filtrate, cooled to 10° C., an excess of a solution of sodium 2-ethylhexanoate in isopropanol is added maintaining the reaction mixture under stirring and at a temperature 10°-5° C. A solid precipitates which is recrystallized from water/acetone and dried under vacuum to give 7-[(1-ethyl-6-fluoro-7-chloro-1,4-dihydro-4-oxoquinolin-3-yl)carboxyamido]cephalosporanic acid sodium salt, mp 160°-170° C. (decomposition).

EXAMPLES 2-4

Operation is carried out according to the previously described procedure and 2) using 1-cyclopropyl-6-fluoro-7-chloro-1,4-dihydro-4-oxoquinoline-3-carboxylic acid and 7-amino-3-[((1H-1,2,3-triazol-5-yl)thio)methyl]ceph-3-em-4-carboxylic acid, 7-[(1-cyclopropyl-6-fluoro-7-chloro-1,4-dihydro-4-oxoquinolin-3-yl)carboxamido]-3-[((1H-1,2,3-triazol-5-yl) thio)methyl]ceph-3-em-4-carboxylic acid, mp 155°–200° C. (decomposition), is obtained;

3) using 1-cyclopropyl-6-fluoro-7-chloro-1,4-dihydro-4-oxoquinoline-3-carboxylic acid and 7-aminocephalosporanic acid, 7-[(1-cyclopropyl-6-fluoro-7-chloro-1,4-dihydro-4-oxoquinolin-3-yl)carboxamido] cephalosporanic acid, mp 156°–200° C. (decomposition), is obtained;

4) using 1-ethyl-6-fluoro-7-chloro-1,4-dihydro-4-oxoquinoline-3-carboxylic acid and 7-amino-3-[((1H-1,2,3-triazol-5-yl)thio)methyl]ceph-3-em-4-carboxylic acid, 7-[(1-ethyl-6-fluoro-7-chloro-1,4-dihydro-4-oxoquinolin-3-yl) carboxamido]-3-[((1H-1,2,3-triazol-5-yl) thio)methyl]-3-cephem-4-carboxylic acid, mp 158°–200° C. (decomposition), is obtained.

EXAMPLE 5

7-[(1-Ethyl-6-fluoro-7-(piperazin-1-yl)-1,4-dihydro-4-oxoquinolin-3-yl)carboxamido]cephalosporanic acid Grams 52.3 of 7-[(1-ethyl-6-fluoro-7-chloro-1,4-dihydro-7-chloro-4-oxoquinolin-3-yl)carboxyamido] cephalosporanic acid are refluxed under stirring with 86 g piperazine for a period of 4 hr., evaporated under vacuum, the residue taken up with approximately 100 ml water and cooled to 5° C. The precipitate is filtered under vacuum, washed with cold water and re-crystallized from a mixture water:acetone (1:1) to give 7-[1-ethyl-6-fluoro-7-(piperazin-1-yl)-1,4-dihydro-4-oxoquinolin-3-yl)carboxamido] cephalosporanic acid, mp 180°–190° C. (decomposition).

Operation is carried out according to the previously described procedure using 1-methylpiperazine and 1-ethylpiperazine instead of piperazine to obtain, respectively:

— 7-[(1-ethyl-6-fluoro-7-(4-methylpiperazin-1-yl)-1,4-dihydro-4-oxoquinolin-3-yl)carboxamido] cephalosporanic acid, — 7-[(1-ethyl-6-fluoro-7-(4-ethylpiperazin-1-yl)-1,4-dihydro-4-oxoquinolin-3-yl)carboxamido] cephalosporanic acid.

EXAMPLE 6

7-[(1-Cyclopropyl-6-fluoro-7-chloro-1,4-dihydro-4-oxoquinolin- 3-yl)carboxamido]cephalosporanic acid.

To 28.2 g 1-cyclopropyl-6-fluoro-7-chloro-1,4-dihydro-4-oxoquinoline-3-carboxylic acid in 180 ml methylene chloride and 20 ml isopropanol is added under stirring a solution of 6.5 g potassium hydroxide in 5 ml water. The mixture is refluxed for 1 hr, then 0,4 ml of a solution of pyridine in isopropanol (3:17) are added thereto cooling to −30° C. Milliliters 11.6 trimethylacetyl chloride are added slowly under stirring to the reaction mixture and stirring and a temperature between −25°/−30° C. are maintained for a further 1½ hr. Temperature is lowered to −40° C. and to the reaction mixture is added slowly under stirring and keeping temperature at −40°/−35° C., first a solution of 25 g 7-aminocephalosporanic acid in 50 ml methylene chloride, 17.5 ml triethylamine and 3 ml distilled water then 1.5 ml 2-ethylhexanoic acid. Stirring is maintained and temperature is allowed to increase in the period of 3 hr. to −30°/−25° C., then 200 ml distilled water are added and the pH value is checked to 8.5–9.5 for indication of completed reaction. It is filtered under vacuum and washed with 50 ml distilled water, then the aqueous and organic phases are separated, the organic layer further washed with 50 ml water and the aqueous layers, collected together, are treated at 15° C. with activated carbon and filtered under vacuum.

The aqueous solution is acidified by slowly adding under stirring hydrochloric acid adjusting the pH to 4.1–4.2. Temperature is maintained at 15°–10° C. and a crystalline compound separates which is filtered under vacuum, washed with 200 ml distilled water and 100 ml isopropanol to give 7-[(1-cyclopropyl-6-fluoro-7-chloro-1,4-dihydro-4-oxoquinolin- 3-yl)carboxamido]cephalosporanic acid, mp 156°–200° C. (decomposition).

EXAMPLE 7

Operation is carried out according to the procedure in Example 5 to obtain:

— 7-[(1-cyclopropyl-6-fluoro-7-(piperazin-1-yl)-1,4-dihydro-4-oxoquinolin-3-yl)carboxamido] cephalosporanic acid, mp 200°–216° C. (decomposition);

— 7-[(1-cyclopropyl-6-fluoro-7-(4-methylpiperazin-1-yl)-1,4-dihydro-4-oxoquinolin-3-yl)carboxamido] cephalosporanic acid;

— 7-[(1-cyclopropyl-6-fluoro-7-(4-ethylpiperazin-1-yl)-1,4-dihydro-4-oxoquinolin-3-yl)carboxamido] cephalosporanic acid, mp 290°–310° C. (decomposition).

EXAMPLE 8

Operation is carried out according to the previously described procedures reacting the suitable 1-substituted 6-fluoro-7-chloro-1,4-dihydro-4-oxoquinoline carboxylic acid in activated form with the corresponding 3-substituted 7-aminoceph-3-em-4-carboxylic acid and optionally replacing 7-Cl with a desired substituent. The following compounds have been prepared:

— 7-[(1-cyclopropyl-6-fluoro-7-chloro-1,4-dihydro-4-oxoquinolin-3-yl)carboxamido]-3-[((1H-1,2,3-triazol-5-yl)thio) methyl]ceph-3-em-4-carboxylic acid, 155°–200° C. (decomposition);

— 7-[(1-cyclopropyl-6-fluoro-7-chloro-1,4-dihydro-4-oxoquinolin-3-yl)carboxamido]-3-[((1-methyl-1H-tetrazol-5-yl) thio)methyl]ceph-3-em-4-carboxylic acid;

— 7-[(1-ethyl-6-fluoro-7-chloro-1,4-dihydro-4-oxoquinolin-3-yl)carboxamido]-3-[((1-methyl-1H-tetrazol-5-yl)thio)methyl]ceph-3-em-4-carboxylic acid;

— 7-[(1-cyclopropyl-6-fluoro-7-chloro-1,4-dihydro-4-oxoquinolin-3-yl)carboxamido]-3-[((5-methyl-1,3,4-thiadiazol-2-yl)thio)methyl]ceph-3-em-4-carboxylic acid;

— 7-[((1-cyclopropyl-6-fluoro-7-(piperazin-1-yl)-1,4-dihydro-4-oxoquinolin-3-yl)carboxamido]-3-[((1H-1,2,3-triazol-5-yl)thio)methyl]ceph-3-em-4-carboxylic acid, mp 250°–260° C. (decomposition);

— 7-[((1-cyclopropyl-6-fluoro-7-(4-methylpiperazin-1-yl)-1,4-dihydro-4-oxoquinolin-3-yl)carboxamido]-3-[((1H-1,2,3-triazol-5-yl)thio)methyl]ceph-3-em-4-carboxylic acid;

— 7-[(1-cyclopropyl-6-fluoro-7-((4-ethylpiperazin-1-yl)-1,4-dihydro-4-oxoquinolin-3-yl)carboxamido]-3-[( (1H-1,2,3-triazol-5-yl)thio)methyl]ceph-3-em-4-carboxylic acid, mp 170°–180° C. (decomposition), is obtained.

— 7-[(1-ethyl-6-fluoro-7-(piperazin-1-yl)-1,4-dihydro-4-oxoquinolin-3-yl)carboxamido]-3-[((1H-1,2,3-triazol-5-yl) thio)methyl]-3-cephem-4-carboxylic acid;

— 7-[(1-ethyl-6-fluoro-7-(4-ethylpiperazin-1-yl)-1,4-dihydro-4-oxoquinolin-3-yl)carboxamido]-3-[((1H-1,2,3-triazol-5-yl)thio)methyl]-3-cephem-4-carboxylic acid;

— 7-[(1-ethyl-6-fluoro-7-(4-methylpiperazin-1-yl)-1,4-dihydro-4-oxoquinolin-3-yl)carboxamido]-3-[((1H-1,2,3-triazol-5-yl)thio)methyl]ceph-3-em-4-carboxylic acid;

— 7-[(1-ethyl-6-fluoro-7-(piperazin-1-yl)-1,4-dihydro-4-oxoquinolin-3-yl)carboxamido]-3-[((1-methyl-1H-tetrazol-5-yl) thio)methyl]ceph-3-em-4-carboxylic acid;

— 7-[(1-ethyl-6-fluoro-7-(4-methylpiperazin-1-yl)-1,4-dihydro-4-oxoquinolin-3-yl)carboxamido]-3-[((1-methyl-1H-tetrazol-5-yl)thio)methyl]ceph-3-em-4-carboxylic acid;

— 7-[(1-ethyl-6-fluoro-7-(4-ethylpiperazin-1-yl)-1,4-dihydro-4-oxoquinolin-3-yl)carboxamido]-3-[((1-methyl-1H-tetrazol-5-yl)thio)methyl]ceph-3-em-4-carboxylic acid;

— 7-[(1-ethyl-6-fluoro-7-chloro-1,4-dihydro-4-oxoquinolin-3-yl)carboxamido]-3-[((2,5-dihydro-6-hydroxy-2-methyl-5-oxo-1,2,4-triazin-3-yl)thio) methyl]ceph-3-em-4-carboxylic acid;

— 7-[(1-cyclopropyl-6-fluoro-7-chloro-1,4-dihydro-4-oxoquinolin-3-yl)carboxamido]-3-[((2,5-dihydro-6-hydroxy-2-methyl-5-oxo-1,2,4-triazin-3-yl)thio) methyl]ceph-3-em-4-carboxylic acid;

— 7-[(1-ethyl-6-fluoro-7-(4-ethylpiperazin-1-yl)-1,4-dihydro-4-oxoquinolin-3-yl)carboxamido]-3-[((2,5-dihydro-6-hydroxy-2-methyl-5-oxo-1,2,4-triazin-3-yl)thio)methyl]ceph-3-em-4-carboxylic acid;

— 7-[(1-cyclopropyl-6-fluoro-7-(4-ethylpiperazin-1-yl)-1,4-dihydro-4-oxo-quinolin-3-yl)carboxamido]-3-[((2,5-dihydro-6-hydroxy-2-methyl-5-oxo-1,2,4-triazin-3-yl)thio)methyl]ceph-3-em-4-carboxylic acid.

I claim:

1. Quinolonylcarboxamidocephalosporin derivatives having the formula:

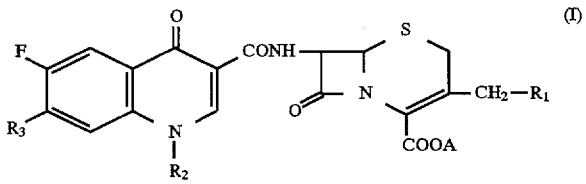

wherein $R_1$ represents hydrogen, acetoxy, carbamyloxy, or an heterocyclic group selected from the group consisting of pyridin-1-yl, 1H-1,2,3-triazol-5-ylthio, 1-methyl-1H-tetrazol-5-ylthio, 5-methyl-1,3,4-thiadiazol-2-ylthio, and 2,5-dihydro-6-hydroxy-2-methyl-5-oxo-1,2,4-triazin-3-ylthio;

$R_2$ represents hydrogen, 1–4 C straight or branched alkyl radical, or 3–5 C cycloalkyl radical;

$R_3$ represents a halogen atom, an heterocyclic group selected from group consisting of piperazin-1-yl, 4-methylpiperazin-1-yl, and 4-ethylpiperazin-1-yl; and A represents hydrogen, an alkaline metal selected from sodium and potassium or an ammonium group.

2. Quinolonylcarboxamidocephalosporin derivatives according to claim 1, wherein $R_2$ represents a cyclopropyl radical or an ethyl radical.

3. Quinolonylcarboxamidocephalosporin derivatives according to claim 1, wherein $R_1$ represents (1H-1,2,3-triazol-5-yl)thio radical.

4. Quinolonylcarboxamidocephalosporin derivatives according to claim 1, wherein $R_1$ represents the acetoxy radical.

5. A quinolonylcarboxamidocephalosporin derivative according to claim 1, which is 7-[(1-Ethyl-6-fluoro-7-chloro-1,4-dihydro-4-oxoquinolin-3-yl)carboxyamido] cephalosporanic acid.

6. A quinolonylcarboxamidocephalosporin derivative according to claim 1, which is 7-[(1-Ethyl-6-fluoro-7-(piperazin-1-yl)-1,4-dihydro-4-oxoquinolin-3-yl) carboxamido]cephalosporanic acid.

7. A quinolonylcarboxamidocephalosporin derivative according to claim 1, which is 7-[(1-Ethyl-6-fluoro-7-(4-ethylpiperazin-1-yl)-1,4-dihydro-4-oxoquinolin-3-yl) carboxamido]cephalosporanic acid.

8. A quinolonylcarboxamidocephalosporin derivative according to claim 1, which is 7-[(1-Cyclopropyl-6-fluoro-7-chloro-1,4-dihydro-4-oxoquinolin-3-yl)carboxamido] cephalosporanic acid.

9. A quinolonylcarboxamidocephalosporin derivative according to claim 1, which is 7-[(1-Cyclopropyl-6-fluoro-7-(piperazin-1-yl)-1,4-dihydro-4-oxoquinolin-3-yl) carboxamido]cephalosporanic acid.

10. A quinolonylcarboxamidocephalosporin derivative according to claim 1, which is 7-[(1-Cyclopropyl-6-fluoro-7-(4-ethylpiperazin-1-yl)-1,4-dihydro-4-oxoquinolin-3-yl) carboxamido]cephalosporanic acid.

11. A quinolonylcarboxamidocephalosporin derivative according to claim 1, which is 7-[(1-Ethyl-6-fluoro-7-chloro-1,4-dihydro-4-oxoquinolin-3-yl) carboxamido]-3-[ (1H-1,2,3-triazol-5-yl)thio)methyl]-3-cephem-4-carboxylic acid.

12. A quinolonylcarboxamidocephalosporin derivative according to claim 1, which is 7-[(1-Ethyl-6-fluoro-7-(piperazin-1-yl)-1,4-dihydro-4-oxoquinolin-3-yl) carboxamido]-3-[((1H-1,2,3-triazol-5-yl)thio)methyl]-3-cephem-4-carboxylic acid.

13. A quinolonylcarboxamidocephalosporin derivative according to claim 1, which is 7-[(1-Ethyl-6-fluoro-7-(4-ethylpiperazin-1-yl)-1,4-dihydro-4-oxoquinolin-3-yl) carboxamido]-3-[((1H-1,2,3-triazol-5-yl)thio)methyl]-3-cephem-4-carboxylic acid.

14. A quinolonylcarboxamidocephalosporin derivative according to claim 1, which is 7-[(1-Cyclopropyl-6-fluoro-7-chloro-1,4-dihydro-4-oxoquinolin-3-yl)carboxamido]-3-[ ((1H-1,2,3-triazol-5-yl)thio)methyl]ceph-3-em-4-carboxylic acid.

15. A quinolonylcarboxamidocephalosporin derivative according to claim 1, which is 7-[((1-Cyclopropyl-6-fluoro-7-(piperazin-1-yl)-1,4-dihydro-4-oxoquinolin-3-yl) carboxamido]-3-[((1H-1,2,3-triazol-5-yl)thio)methyl]ceph-3-em-4-carboxylic acid.

16. A quinolonylcarboxamidocephalosporin derivative according to claim 1, which is 7-[(1-Cyclopropyl-6-fluoro-7-(4-ethylpiperazin-1-yl)-1,4-dihydro-4-oxoquinolin-3-yl) carboxamido]-3-[((1H-1,2,3-triazol-5-yl)thio)methyl]ceph-3-em-4-carboxylic acid.

17. A quinolonylcarboxamidocephalosporin derivative according to claim 1, which is 7-[(1-Ethyl-6-fluoro-7-(4-methylpiperazin-1-yl)-1,4-dihydro-4-oxoquinolin-3-yl) carboxamido]cephalosporanic acid.

18. A quinolonylcarboxamidocephalosporin derivative according to claim 1, which is 7-[(1-Cyclopropyl-6-fluoro-7-(4-methylpiperazin-1-yl)-1,4-dihydro-4-oxoquinolin-3-yl)carboxamido]cephalosporanic acid.

19. A quinolonylcarboxamidocephalosporin derivative according to claim 1, which is 7-[((1-Cyclopropyl-6-fluoro-7-(4-methylpiperazin-1-yl)-1,4-dihydro-4-oxoquinolin-3-yl)carboxamido]-3-[((1H-1,2,3-triazol-5-yl)thio)methyl]ceph-3-em-4-carboxylic acid.

20. A quinolonylcarboxamidocephalosporin derivative according to claim 1, which is 7-[(1-Ethyl-6-fluoro-7-(4-methylpiperazin-1-yl)-1,4-dihydro-4-oxoquinolin-3-yl)carboxamido]-3-[((1H-1,2,3-triazol-5-yl)thio)methyl]ceph-3-em-4-carboxylic acid.

21. A quinolonylcarboxamidocephalosporin derivative of claim 1, wherein $R_1$ is 1-methyl-1H-tetrazol-5-ylthio; $R_2$ is a 3–5 C cyclo alkyl radical; $R_3$ is ethylpiperazin-1-yl, and A is hydrogen.

22. A pharmaceutical composition comprising a therapeutically effective amount of one or more compounds according to any one of claims 1–20, or 21 in admixture with a suitable pharmaceutically acceptable diluent.

* * * * *